United States Patent
Dick et al.

(10) Patent No.: US 9,877,870 B2
(45) Date of Patent: Jan. 30, 2018

(54) DEVICE AND METHOD FOR CONTROLLING A LASER SYSTEM

(75) Inventors: Manfred Dick, Gefell (DE); Dieter Grebner, Grossloebichau (DE); Matthias Reich, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 1178 days.

(21) Appl. No.: 13/701,466

(22) PCT Filed: Jun. 1, 2011

(86) PCT No.: PCT/EP2011/002709
§ 371 (c)(1),
(2), (4) Date: Nov. 30, 2012

(87) PCT Pub. No.: WO2011/151063
PCT Pub. Date: Dec. 8, 2011

(65) Prior Publication Data
US 2013/0085480 A1     Apr. 4, 2013

(30) Foreign Application Priority Data
Jun. 3, 2010 (DE) .......... 10 2010 022 634

(51) Int. Cl.
*A61F 9/008* (2006.01)

(52) U.S. Cl.
CPC ............ *A61F 9/0084* (2013.01); *A61F 9/008* (2013.01); *A61F 9/00838* (2013.01); *A61F 2009/0087* (2013.01); *A61F 2009/00844* (2013.01); *A61F 2009/00851* (2013.01)

(58) Field of Classification Search
CPC .... A61F 2009/00844; A61F 2009/0087; A61F 9/008; A61F 9/00838; A61F 9/0084
See application file for complete search history.

(56) References Cited

U.S. PATENT DOCUMENTS

| | | |
|---|---|---|
| 2005/0165387 A1 | 7/2005 | Lubatschowski et al. |
| 2006/0106371 A1 | 5/2006 | Muhlhoff et al. |
| 2008/0021443 A1 | 1/2008 | Bischoff et al. |
| 2008/0058734 A1 | 3/2008 | Hanft et al. |

(Continued)

FOREIGN PATENT DOCUMENTS

| | | |
|---|---|---|
| DE | 103 23 422 A1 | 4/2004 |
| DE | 103 58 927 A1 | 7/2005 |

(Continued)

OTHER PUBLICATIONS

European Laser Safety Standard DIN EN 60825-1, dated Aug. 2001, 122 pages.

*Primary Examiner* — Scott T Luan
(74) *Attorney, Agent, or Firm* — Patterson Thuente Pedersen, P.A.

(57) ABSTRACT

A device and a method for controlling a laser system for the treatment of the eye lens by means of laser-induced disruptions. The laser system includes a femtosecond laser and a deflection unit for directing the laser beam and a detection device for detecting a value characteristic of the occurrence of disruptions being provided. The detection device is connected to the control device and the control device is adapted to determine a pulse energy for the laser system from the characteristic value and to actuate the laser accordingly.

11 Claims, 1 Drawing Sheet

(56) References Cited

U.S. PATENT DOCUMENTS

| | | |
|---|---|---|
| 2009/0143772 A1* | 6/2009 | Kurtz .................. A61F 9/008 606/4 |
| 2009/0171327 A1 | 7/2009 | Kurtz et al. |
| 2009/0294422 A1 | 12/2009 | Lubatschowski et al. |
| 2010/0191230 A1 | 7/2010 | Dick et al. |
| 2011/0276042 A1 | 11/2011 | Dick et al. |

FOREIGN PATENT DOCUMENTS

| | | |
|---|---|---|
| DE | 10 2005 032 946 A1 | 2/2006 |
| DE | 11 2008 002 380 T5 | 6/2010 |
| EP | 1 663 087 B1 | 3/2011 |
| WO | WO 2005/011544 A1 | 2/2005 |
| WO | WO 2005/070358 A1 | 8/2005 |
| WO | WO 2006/074469 A2 | 7/2006 |
| WO | WO 2007/022948 A2 | 3/2007 |
| WO | WO 2008/017428 A2 | 2/2008 |
| WO | WO 2009/039315 A2 | 3/2009 |

\* cited by examiner

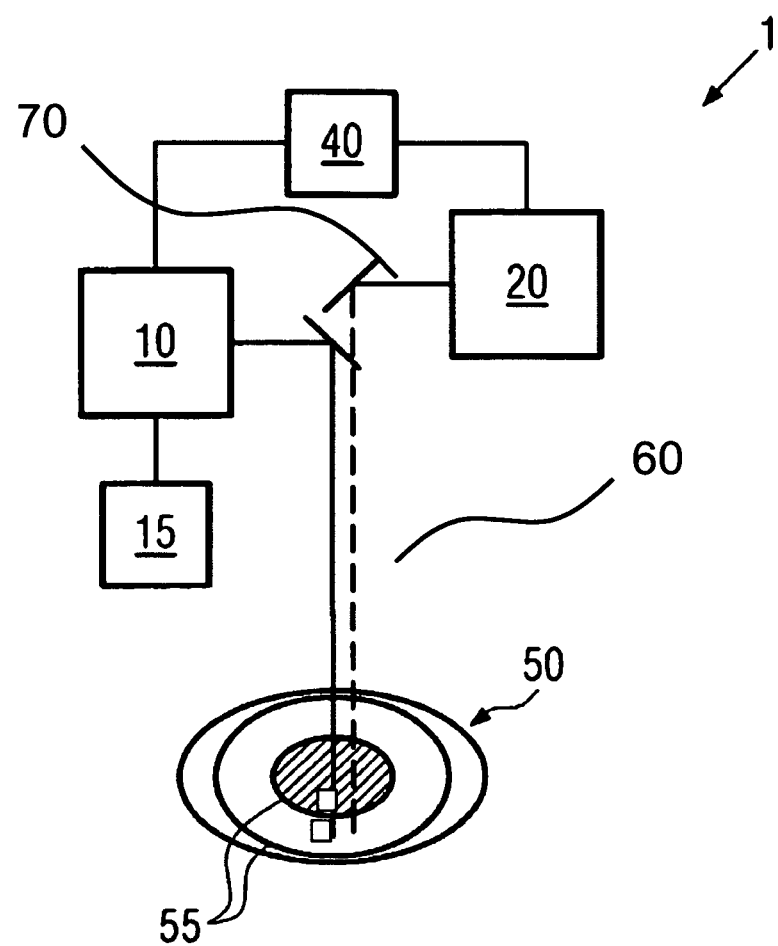

DEVICE AND METHOD FOR CONTROLLING A LASER SYSTEM

PRIORITY CLAIM

The present application is a National Phase entry of PCT Application No. PCT/EP2011/002709, filed Jun. 1, 2011, which claims priority from German Application No. 10 2010 022 634.3, filed Jun. 3, 2010, the disclosures of which are hereby incorporated by reference herein in their entirety.

FIELD OF THE INVENTION

The invention relates to a device and a method for controlling a laser system, particularly in femtosecond laser surgery of tissue, preferably of the human crystalline lens.

BACKGROUND

It is known that with the help of femtosecond laser radiation, non-linear interactions and, at higher pulse energies or energy densities, a photodisruption in particularly optical materials or tissue can be generated.

In everyday clinical life, for example, this is utilized in eye-surgical lasers such as the "Visumax" from Carl Zeiss Meditec AG.

Here the laser system is provided with an fs laser beam source, the pulse energy of which is adjusted beforehand at a predetermined repetition rate (e.g. 500 kHz) of the laser pulses in a relevant range of, e.g. 50 nJ-5 µJ in order to always reliably generate a photodisruption in the tissue. With regard to a treatment of the cornea of the eye, the variance of the tissue properties of the individual patients is relatively low, and therefore a pulse energy of, e.g. 0.5 or 1 µJ will most certainly lead to a disruption.

However, for the treatment of a human crystalline lens aged due to presbyopia or cataract, it can be determined visually that the scattering and/or absorption properties vary from good transparency to complete opacity. Accordingly, the pulse energy value required for the photodisruptive treatment is doubtful and uncertain.

Therefore, the threshold energy for generating photodisruptions in the lens is locally subject to great fluctuations and as a result, only unsatisfactory treatment results can be achieved with a specified energy.

EP 1 663 087 discloses such an fs-laser system for treating the crystalline lens and cites a pulse energy in the range from 1 pJ to 500 nJ, i.e. a range of more than 5 magnitudes. No additional specifics are provided.

Alternatively, the overall energy applied in the eye should be as low as possible in order to safely avoid unwanted side effects, such as damage to the retina.

WO 2008/017428 by the applicant, the entire content of which is hereby incorporated by reference, describes a laser phaco system having an fs laser and a detector for acquiring the geometry of the crystalline lens in order to ensure a precise navigation within the lens. Among others, the following detector for acquiring the geometry are cited: Devices on the basis of optical coherence tomography (OCT), rotating slit Scheimpflug cameras, confocal laser scanners, and ultrasonographs. A further analysis of the tissue to be treated is not disclosed.

SUMMARY OF THE INVENTION

Therefore, the problem addressed by the invention is that of providing a solution for obtaining optimal treatment parameters for the treatment of a crystalline lens.

This problem is solved by either determining the local tissue properties such as absorption or scattering using an advance diagnosis and thus predict the laser threshold to be expected, or by determining the actual occurrence of a photodisruption of the tissue, using online diagnostics. Based on these values, the energy and/or the spot distance of the fs laser radiation are adjusted within a safe range, preferably above the disruption threshold.

Care is taken that the surgical result is ensured and the laser energy is not adjusted at too high a level which could cause unwanted side effects, e.g., damage to the retina.

The method according to the invention and the corresponding device for carrying out these individually adjusted therapies are further described in the following paragraphs.

In order to predict a local threshold energy, the measurement of one or several of the following material properties is provided, according to the invention: Scattering, absorption, or hardness of the tissue. The tissue condition is characterized spatially resolved in all three dimensions. Suitable measurement methods for this purpose are, e.g., optical coherence tomography, Scheimpflug photography, microscopy, confocal detection, and interferometric or acoustic hardness measurements.

Also of use is a two-dimensionally, spatially resolved measurement of the scattering of the eye within the pupil opening, e.g., using a Shack-Hartman sensor. As is known, this method at first generates wavefront data of the eye which influence the spot diameter of the therapeutic laser beam and thus also the threshold of the optical breakthrough. When the therapy beam is guided across an adaptive mirror, the wavefront of which is controlled online with the data of the Shack-Hartman wavefront sensor, it is always possible to adjust a laser spot to its minimum. If no compensation with adaptive optics is carried out, the pulse energy and/or the spot distance can be adjusted to the corresponding spot diameter in order to adjust an optimal local optical breakthrough due to the local refractive properties in the eye. The analysis of the structure of the individual spots and the substrate on the CCD chip of the Shack-Hartmann sensor also provides a measure for the two-dimensionally, spatially resolved scattering of the individual eye of the patient which leads to a local decrease of the energy input in the focal point of the therapy laser beam. With the help of these data, the pulse energy and/or the spot distance can also be readjusted in order to adjust an optimal, local optical breakthrough.

From one or several of these measured variables, which are preferably determined prior to the treatment of the eye of the patient, predictions about the threshold parameters for the therapy can be obtained, using theoretical modelings or even empirical relationships, and, e.g., combined in a three-dimensional chart or mathematical approximation function. Said modelings take into account particularly the optical attenuations and wavefront distortions of the focused light on its way through the eye to the treatment point. The ray-tracing method e.g., is a suitable modeling technique. With said method, the intensities of the laser light in the focus can be calculated, among others. By approximation, the disruption threshold for a given laser beam source is connected to a constant intensity value.

From the individual distribution of the treatment thresholds in the crystalline lens thus obtained, optimized control data for the laser therapy are derived. During determination of the control data, it is also taken into account that an overlapping of the focal volume of consecutive laser pulses leads to a reduction of the threshold energy. This connection e.g., is shown in patent document WO2007/022948, the entire content of which is hereby incorporated by reference.

The patient-specific control data thus obtained determine a spatial and temporal sequence of the applied pulse energies and spot distances. Said control data are used for controlling the laser beam source, the pulse pickers, the attenuators and the scanner systems. A pulse picker is described in DE 103 58 927.

In addition to taking into account a prediction of the treatment thresholds, the treatment parameters can—alternatively or in combination—be measured and controlled online in order to reach an optimal therapy. One or several measured variables which characterize the treatment process are recorded and evaluated during treatment and the laser parameters are, accordingly, continuously corrected. E.g., the intensity of the plasma sparks during the disruption can be such a measured variable which can be separated from the laser wavelength using suitable filters and measured with sensitive optical detectors. The forming of transient or stable bubbles is also an indicator for the disruption and can preferably be quantified using interferometric methods. The disruption leads to a separation of the tissue and thus locally changes the scattering properties. A suitable measurement method, e.g., is the confocal detection, wherein the linear or non-linear (e.g., SHG) scattering can be changed.

A further possible measured variable is the change of the absorption properties. It is known that with age, the crystalline lens increasingly absorbs in the blue spectral range and that said absorption can be reduced with intensive laser radiation. Such a change can be detected with a confocal measuring configuration.

Furthermore, inferences about the treatment effect can be derived from the intensity of the backscattered treatment light. Once again, a confocal detection can preferably be used for the measurement. Since the measuring signals of many of the above variables or measurement methods are relatively small, the detection systems can be combined with known methods for improving the signal-to-noise ratio. Frequently, this requires an averaging over a number of pulses or measuring cycles. Known systems, e.g., are the lock-in amplifier or the boxcar integrator.

In order to sensitively detect the change of a measured variable, which is induced by the treatment, a direct comparison measurement can, according to the invention, be carried out between two different locations (known as "dual beam"), wherein one of the measuring locations has been treated and the other measuring location has not yet been treated.

It can also be advantageous to vary the treatment energy between two consecutive pulses or pulse cycles by a constant value and thus selectively detect a change in said energy interval. This is particularly effective when the measuring signal at the treatment threshold abruptly changes its value and is to be adjusted to a value near said threshold.

The measurement values cited above are used to build up a control loop and to obtain a constant treatment result independently of the local tissue properties. The applied pulse energy and/or spot distance are used as control variables.

In addition to a maximal therapy effect, an optimal treatment system must also ensure sufficient protection of the surrounding ocular tissue, particularly the retina, from unwanted damages. Therefore, retinal irradiances must be observed which are specified in the laser safety standards.

In accordance with the European Laser Safety Standard DIN EN 60825-1, the most restrictive boundary for the safe use of femtosecond laser radiation is the following limit: $E_{limit,\ pulse\ sequence} = E_{single\ pulse} * N^{-1/4}$, with $E_{single\ pulse}$ being the energy of a single laser pulse and N the number of laser pulses. According to the invention, the energy of the impinging laser radiation is narrowed to energy values $E < E_{limit,\ pulse\ sequence}$.

For this purpose, $E_{single\ pulse}$ is specifically specified by a control unit. In addition, $E_{single\ pulse}$ is measured or determined by measuring the laser pulse repetition frequency and the mean laser power.

Furthermore, the number of the laser pulses to be applied is determined on the basis of the calculated application result (therapy pattern). As a result, the maximal total energy which is introduced into the eye does not exceed the value from the laser standard $E_{limit,\ pulse\ sequence}$, when the control data record for the therapy process is determined.

In order to ensure that said value is effectively observed during therapy, a counting device is additionally integrated in the laser therapy device and the actually impinging laser pulses are registered. The maximally permissible number of impinging pulses is calculated with the known single pulse energy, the actually applied pulses are measured and the laser radiation deactivated once the limit is reached. Thus a safety function is implemented which ensures the safety of the retina even with an error in the calculation of the control data. Contrary to known safety mechanisms, the proposed method allows for an approach close to the permissible threshold values.

The described methods can be used particularly advantageously for the laser treatment of the human crystalline lens, particularly with ultrashort laser pulses. However, the invention also relates to other laser applications in ophthalmology, for example, to the treatment of the retina or cornea (e.g., in keratoplasty).

In conclusion, the invention is characterized by a device and a method for three-dimensional scanner-guided focusing of fs-laser radiation during which a data record relevant for the dosimetry of the laser radiation is ascertained using a previous 3D analysis of the volume provided for the treatment and said data record is used for the three-dimensional, dynamic control of the laser parameters (particularly energy and/or spot distance). The invention provides for the detection of the development of disruption bubbles using an online diagnosis, and a value range for the laser parameters (particularly pulse energy and/or spot distance) is adjusted. Moreover, the counting of the applied laser pulses ensures that damage to the eye is avoided.

The invention is also characterized by a device and a method for treating ocular tissue with ultrashort laser radiation, wherein the eye or part of the eye, prior to the generation of control data, is measured with an optical method, a variation of the threshold values to be expected for the treatment parameters is determined using the volume to be treated and a set of control data is derived therefrom for the application of the laser pulses. An optical signal is recorded during the application of the laser pulses which is characteristic for the strength of the treatment process, and one process parameter is changed for the subsequent laser pulses in accordance to a predefined function on the basis of the strength of the optical signal. Moreover, the number and/or the entire energy of the impinging laser pulses is measured during the application of the laser pulses, the measured value is continuously compared to a reference value and the emerging laser radiation is deactivated once the threshold value is reached or exceeded.

BRIEF DESCRIPTION OF THE DRAWING

In the following, the invention is further described with the drawing.

The FIGURE is a schematic depiction of a treatment device 1 according to the present invention.

DETAILED DESCRIPTION

The treatment device 1 comprises a detection device 10, having an optical, confocal and/or optical coherence tomography device and/or wavefront-determining sensors 15. In addition, a processing laser 20 is provided. The detection device 10 and the processing laser 20 are connected to a control device 40. A corresponding optical path can be directed from the detection device 10 and the processing laser 20 via scanner mirrors into an optical element 50, in this case a multilayered lens. Individual volume elements in the lens 50 are denoted with the reference sign 55. The processing laser 20 is an fs laser with a pulse duration of 300 fs, and the laser beam 60 of said fs laser can be guided three-dimensionally by a deflection unit 70 over the element 50 to be treated. The inner structure comprising a plurality of volume elements 55 of the lens 50 are detected using the detection device 10. The sensors 15 are supporting said detection and determine once again a three-dimensional image of said inner structure. This information is transmitted to the control device 40 which calculates firing coordinates (and thus the spot distances) for the processing laser 20 using, e.g., a finite element model.

Particularly preferred, the data are first transmitted to the control device for calculating preferred incision geometries which, e.g., lead to an increase of the accommodative capacity when applied into the eye. For example, with the finite element method, a pattern can be determined which promises the highest accommodative increase. Once the simulation is concluded, firing parameters are provided for subsequently applying said incision geometries in the optical element or the crystalline lens using the laser. The control device transmits said data to the processing laser 20 which initiates the correspondingly predetermined treatment of the lens 50. This allows for therapeutic incisions which are generated using bubble fields generated by disruptions of an ultrashort pulse laser system used as processing laser 20. Alternatively, the entire lens can be destroyed with the incisions in order to be subsequently suctioned off in a generally known manner and replaced with an intraocular lens. The scattering properties of the volume element 55 of the lens to be treated are also, as previously described, determined three-dimensionally using the sensors 15, and a preferred value for the pulse energy of the treatment laser is derived from said properties. Said value is subsequently adjusted on the laser in a suitable manner by the control device 40 during the treatment of the corresponding volume element 55.

Moreover, the control device 40 monitors the impinged total energy in order to prevent the permissible dose to be exceeded.

The inveention claimed is:

1. A device for controlling a laser system for treating a crystalline lens using laser-induced disruptions, wherein the laser system comprises a femtosecond laser and a three dimensional scanner that guides a laser beam produced by the femtosecond laser, comprising:
   an optical detection device that determines a characteristic variable that is characteristic for the occurrence of disruptions; and
   an electronic control device;
   wherein the optical detection device is operably connected to the control device and the electronic control device determines a pulse energy, a number of laser pulses applied to one spot position, a laser spot overlap, a laser spot distance or a combination of the foregoing for the laser system from the characteristic variable and controls the laser accordingly.

2. The device according to claim 1, wherein the characteristic variable is a variable selected from the group consisting of scattering, absorption, and tissue hardness.

3. The device according to claim 1, wherein the characteristic variable is detected three-dimensionally and the electronic control device takes said three-dimensionality into account.

4. The device according to claim 1, wherein the characteristic variable is detected prior to or during the treatment.

5. A method for controlling a laser system for treating the crystalline lens using laser-induced disruptions, wherein the laser system comprises a femtosecond laser, the method comprising:
   detecting at least one variable characteristic for the occurrence of disruptions;
   adjusting pulse energy and/or spot distance of the laser pulses accordingly based on the at least one variable characteristic to obtain adjusted values, the spot distance of the laser pulses being a distance between adjacent applied laser pulses; and
   carrying out the treatment with said adjusted values.

6. The method according to claim 5, further comprising selecting the characteristic variable from a group consisting of scattering, absorption, and tissue hardness.

7. The method according to claim 5, further comprising detecting the characteristic variable three-dimensionally and taking said three-dimensionality into account.

8. The method according to claim 5, further comprising detecting the characteristic variable prior to or during treatment.

9. The method according to claim 5, further comprising monitoring impinging pulse energy.

10. A device for controlling a laser system for treating a crystalline lens using laser-induced disruptions, wherein the laser system comprises a femtosecond laser and a three dimensional scanner for guiding the laser beam, comprising:
    an optical detection device that determines a variable characteristic for the occurrence of disruptions; and
    an electronic control device;
    wherein the optical detection device is operably connected to the control device which determines a single pulse energy $E_{single\ pulse}$ and a number of laser pulses N from the characteristic variable, wherein the product of the single pulse energy $E_{single\ pulse}$ and $N^{-1/4}$ does not exceed the energy value $E_{limit,\ pulse\ sequence}$.

11. The device according to claim 10, further comprising a counting device that registers actually impinging laser pulses.

* * * * *

UNITED STATES PATENT AND TRADEMARK OFFICE
CERTIFICATE OF CORRECTION

PATENT NO. : 9,877,870 B2
APPLICATION NO. : 13/701466
DATED : January 30, 2018
INVENTOR(S) : Manfred Dick et al.

It is certified that error appears in the above-identified patent and that said Letters Patent is hereby corrected as shown below:

In the Claims

Column 5, Line 59, delete "inveention" and insert --invention--

Signed and Sealed this
Eleventh Day of December, 2018

Andrei Iancu
*Director of the United States Patent and Trademark Office*